(12) United States Patent
Chammas

(10) Patent No.: US 7,236,694 B1
(45) Date of Patent: Jun. 26, 2007

(54) BLOOD AND BIOLOGICAL FLUID WARMER

(76) Inventor: Jacques Chammas, 14 Pheasant Hill Rd., Walpole, MA (US) 02081

( * ) Notice: Subject to any disclaimer, the term of this patent is extended or adjusted under 35 U.S.C. 154(b) by 0 days.

(21) Appl. No.: 11/340,437

(22) Filed: Jan. 27, 2006

(51) Int. Cl.
*A61F 7/00* (2006.01)
(52) U.S. Cl. .................................. 392/470; 604/113
(58) Field of Classification Search ............ None
See application file for complete search history.

(56) References Cited

U.S. PATENT DOCUMENTS

| | | | |
|---|---|---|---|
| 3,590,215 A | 6/1971 | Anderson et al. | |
| 4,314,143 A | 2/1982 | Bilstad et al. | |
| 4,532,414 A | 7/1985 | Shah et al. | |
| 4,707,587 A | 11/1987 | Greenblatt | |
| 4,747,826 A | 5/1988 | Sassano | |
| 4,759,749 A | 7/1988 | Verkaart | |
| 4,878,537 A | 11/1989 | Verkaart | |
| 4,906,816 A | 3/1990 | van Leerdam | |
| 4,926,830 A | 5/1990 | McNelley | |
| 5,063,994 A | 11/1991 | Verkaart | |
| 5,097,898 A | 3/1992 | Verkaart | |
| 5,125,069 A | 6/1992 | O'Boyle | |
| 5,180,896 A | 1/1993 | Gibby et al. | |
| 5,254,094 A * | 10/1993 | Starkey et al. | 604/113 |
| 5,381,510 A | 1/1995 | Ford et al. | |
| 5,417,274 A | 5/1995 | Verkaart | |
| 5,420,962 A * | 5/1995 | Bakke | 392/470 |
| 5,875,282 A | 2/1999 | Jordan et al. | |
| 6,035,102 A | 3/2000 | Bakke | |
| 6,047,108 A | 4/2000 | Sword et al. | |
| 6,488,659 B1 * | 12/2002 | Rosenman | 604/113 |
| 6,608,968 B2 | 8/2003 | Bakke | |
| 6,629,946 B2 | 10/2003 | Fressinet et al. | |
| 6,882,797 B2 | 4/2005 | Stewart et al. | |

* cited by examiner

*Primary Examiner*—Thor Campbell
(74) *Attorney, Agent, or Firm*—Rissman Jobse Hendricks & Oliverio, LLP

(57) ABSTRACT

This invention is based on combining dual heating means to warm the infused blood or other fluids to a normal body temperature and to compensate for any heat loss from the intravenous line. The infusate is directly heated to a normothermic temperature inside the apparatus as it flows in a plastic pouch having a winding shape passage.

A particular object of the present invention is to provide a new and improved intravenous line heat exchanger to further warm the infusate at high flow rates, or to compensate for any heat loss to the environment at low or stagnant flow rates. The present invention provides a closed circuit heating fluid for the intravenous heat exchanger. The heated fluid used to warm the infusate in the intravenous line is maintained in a clean and isolated circuit. Either dray or wet fluids are used to warm the infusate in the intravenous line heat exchanger. The wet warming fluid is supplied in a disposable pouch fitted inside a warming chamber and integrated with the intravenous line. A peristaltic pump is used to drive the warming fluid in a closed circuit between the pouch and the heat exchanger. The wet fluid remains in the closed circuit, and does not contact the apparatus preventing any build up of mold or fungus. The closed fluid circuit eliminates the need for unnecessary cleaning and periodic maintenance as it is done to the conventional water tank in the existing blood warmers.

11 Claims, 9 Drawing Sheets

BLOOD AND BIOLOGICAL FLUID WARMER

FIELD OF THE INVENTION

This invention relates to the warming of the blood or irrigation fluid to the normal body temperature during infusion process.

BACKGROUND OF THE INVENTION

Blood warming devices have been used in multiple surgeries and trauma cases to warm blood or other physiological or crystalloid fluids to body temperature prior infusion. Blood warming devices are used to bring up the patient body temperature to a normothermic level during surgery or as a response to hypothermia.

Many blood warmers are based on the concept of warming the infusate as it flows through a heat exchanging means or a direct heating means embedded in the system. As the warmed infusate exits the heating system it flows through an intravenous tube accessing the patient. The intravenous tube is typically few feet long extending from the heating system with its distal end connected to the patient. The tube is generally exposed to the environment causing heat to be dissipated by convection.

The blood warmer described in U.S. Pat. No. 5,063,994 heats the blood as it flows to the patient through the intravenous line. This system has the advantage of avoiding any heat loss to the environment, but its warming means is limited to the surface area of the extruded plastic heat exchanger. This limitation impairs the effectiveness of this system and restricts its usage to the low flow applications.

Many attempts were made to develop an effective blood warming system in combination with a thermally protected intravenous line to deliver warmed fluids at high and low flow rates. U.S. Pat. No. 5,417,274 combines a system having a heat exchanging means with a blood warming intravenous line to effectively warm infused blood. This system requires periodic maintenance because of its open system water tank.

The system described in U.S. Pat. No. 5,420,962 heats the infused fluid to the normothermic temperature inside the apparatus then utilizes a corrugated hose to envelope the intravenous line with a jet of hot air flowing inside. The hot air flows from the apparatus through the hose and exits out to the environment at the patient's end. The air hose protects the thermal integrity of the intravenous line, but the exiting flow of hot air to the environment is irritating to the patient and the surgeon. Moreover, the noise generated by the exiting air right at the patient's site is very annoying to the surgical staff.

U.S. Pat. No. 6,608,968 combines the heating of the blood as it flows through the system with the protection of the blood line from heat loss as it flows through the patient line. This method utilizes an elongated sleeve that is equipped with an electric heater. The sleeve is mounted on the warmed blood tubing as it exits the main heating module. The blood tubing has the same structure as the coaxial heat exchanger described in U.S. Pat. No. 5,063,994. In this configuration, the blood flows in the central channel that is surrounded by two half-donut channels. Still air in these outer channels act as an insulator preventing any heat loss from the blood in the central channel to the environment. The heating sleeve is awkward to use and increases the weight and the rigidity of the intravenous line that makes difficult to handle.

There is a need for an efficient fluid warmer for high and low flow rates, combined with a simple and effective intravenous line warmer to compensate for the heat loss at low flow rate, using a single low cost disposable set.

DISCLOSURE OF THE INVENTION

It is a general object of the present invention to provide a new and improved apparatus for warming blood and other physiological, colloid, or crystalloid fluids, and maintain its temperature at the point of infusion into the human body; using a single low cost disposable.

This invention is based on combining dual heating means to warm the infused blood or other fluids to a normal body temperature and to compensate for any heat loss from the intravenous line. The infusate is directly heated to a normothermic temperature inside the apparatus as it flows in a plastic pouch having a winding shape passage communicating with flexible inlet and outlet tubes. As the heated fluid exits the winding path pouch, it is directed to flow inside an intravenous line heat exchanger. A particular object of the present invention is to provide a new and improved intravenous line heat exchanger to further warm the infusate to bring it to a normothermic temperature, or to compensate for any heat loss to the environment at high and low flow rates. The intravenous line is simply made by having the infusate carrying tube submerged in a flow of a warming fluid confined inside a larger tube having both ends sealed by special caps. A third tube is inserted in the larger tube extending along the infusate carrying tube and having its distal end open to the interior of the larger tube. The third tube is used to introduce the warming fluid inside the larger tube or to retrieve it from. The distal end cap seals the warming fluid inside the larger tube allowing for the infusate carrying tube to pass through and reach the infusing site. The proximal end cap allows the infusate tube and the warming fluid supplying tube to pass through to the inside of the larger tube. The proximal cap has a special port communicating by a connected tube to the warming fluid source. This port is used to circulate the warming fluid from the larger tube back to the warming fluid source or in the inverse direction.

It is another object of the present invention to provide a closed circuit heating fluid for the intravenous heat exchanger. The heated fluid used to warm the infusate in the intravenous line is maintained in a clean and isolated circuit. If a dry fluid is used, such as air, the fluid is heated in a closed chamber and recirculated in the intravenous line to warm the infusate. If a wet fluid is used, such as water, the fluid is heated in a pouch that is connected to the intravenous line and recirculates to warm the infusate. The pouch containing the wet fluid is an integrated part of the disposable and it is discarded after use with the rest of disposable set. The wet fluid does not contact the apparatus preventing any build up of mold or fungus and eliminates the need for unnecessary cleaning and periodic maintenance as it is done to the conventional water tank in the existing blood warmers.

For the wet fluid application, a limited basis reusable pouch equipped with means to add fluid is also considered to add flexibility to the system and reduce the disposable cost. This reusable pouch can be used for a limited number of runs, and then be disposed off. The reusable pouch eliminates the need for periodic maintenance and prevents any bacteria or fungus buildup in the system.

DEFINITIONS

Infusate: Is the fluid that is warmed using this system when it is being infused into a patient. This could be but not limited to blood, Plasma, saline, or any crystalloid or colloid solutions that are infused to a patient.

Warming Fluid: Is the fluid that is heated inside the device and then used to warm the infusate inside a heat exchanger. This could be but not limited to water, air, oil, or saline.

DETAILED DESCRIPTION OF THE SYSTEM

Figure 1:
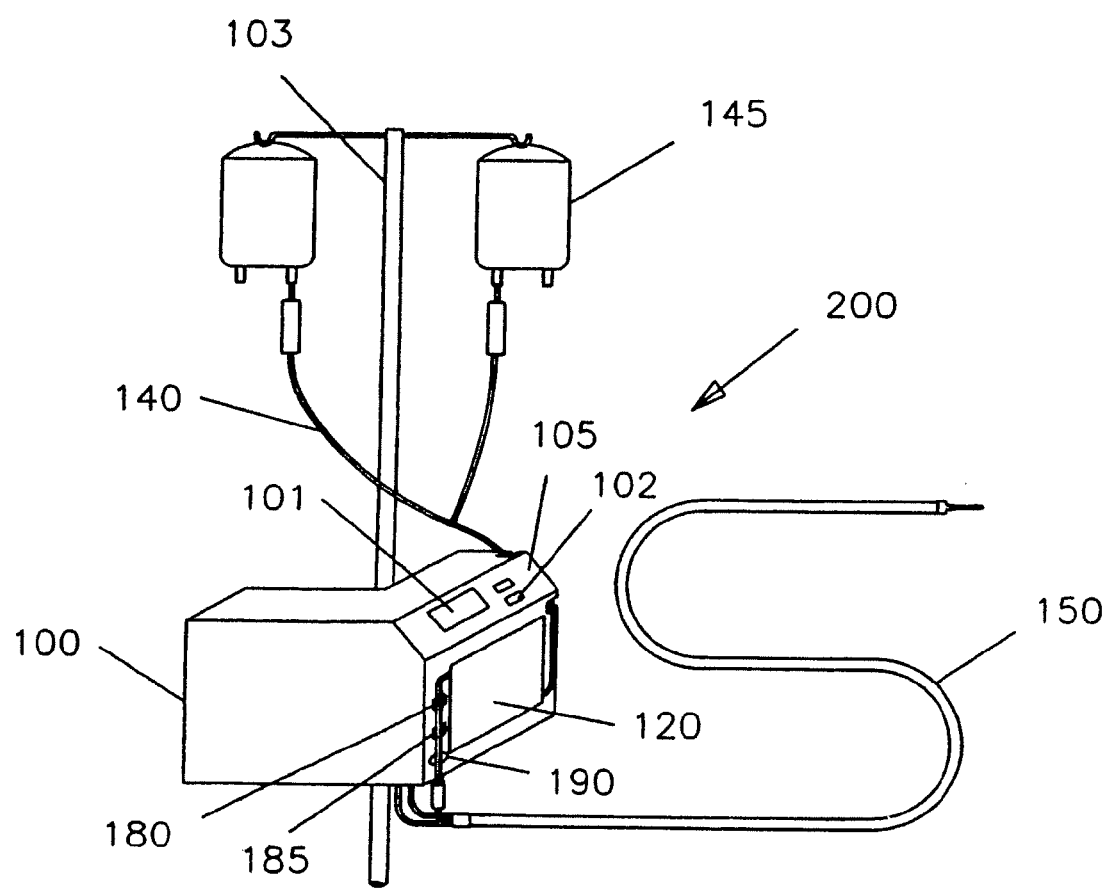
FIG. 1—Blood Warming System—Device and Disposable mounted on IV-pole
Figure 2:
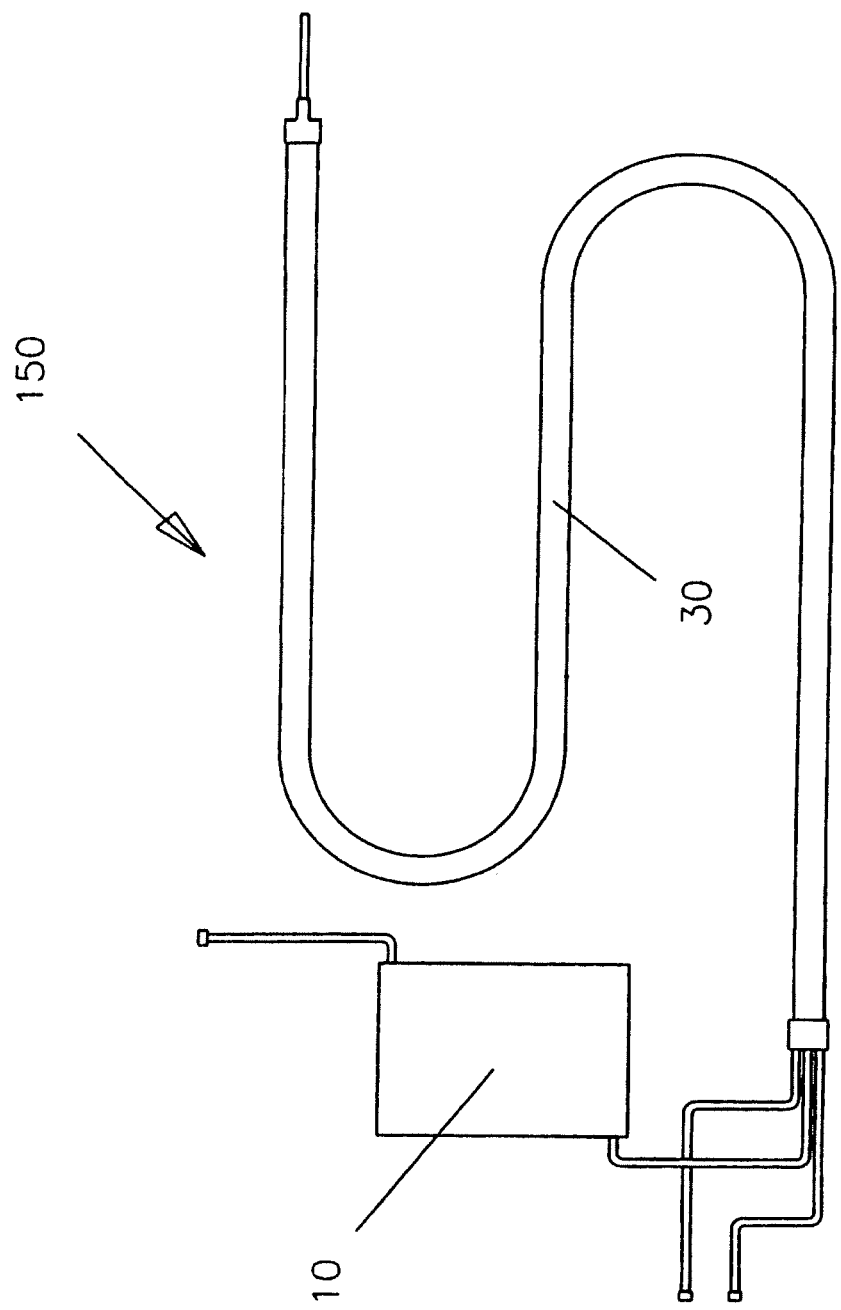
FIG. 2—Blood Warming disposable set, Schematic View

FIG. 1 demonstrates the Blood Warming System 200 encompassing a Blood Warming Device 100 and a Blood Warming Disposable set 150 connected to a Transfer Set 140. Cold blood or biological fluid bags 145 are hanging on an IV-pole 103. A transfer set 140 is used to connect the cold blood bags to the Blood Warmer disposable set. The set has a connection means to aseptically connect to the transfer set. The flow of the cold blood starts from the hanging bags on the IV pole and moves through the transfer set connected to the disposable set. As the blood enters the set it flows inside the Primary Warmer 10 (see FIG. 2) that is mounted inside the Warming Device 100 and sandwiched between two plates maintained at a steady temperature. The blood follows a serpentine path inside the Primary Warmer long enough to raise its temperature to the needed level. The blood exits the Primary Warmer and flows through a tubing that is connected to the Intravenous Line 30. The blood enters the intravenous line 30 and flows through a tubing that is submerged inside a larger tube containing warm flowing fluid. The function of the intravenous line is to maintain the blood temperature at the normal level for low flow rates; and to perform as a secondary warmer for high flow rates. In both high and low flow rates, the temperature of the blood at the infusion point is at the normal body temperature level.

Figure 3:
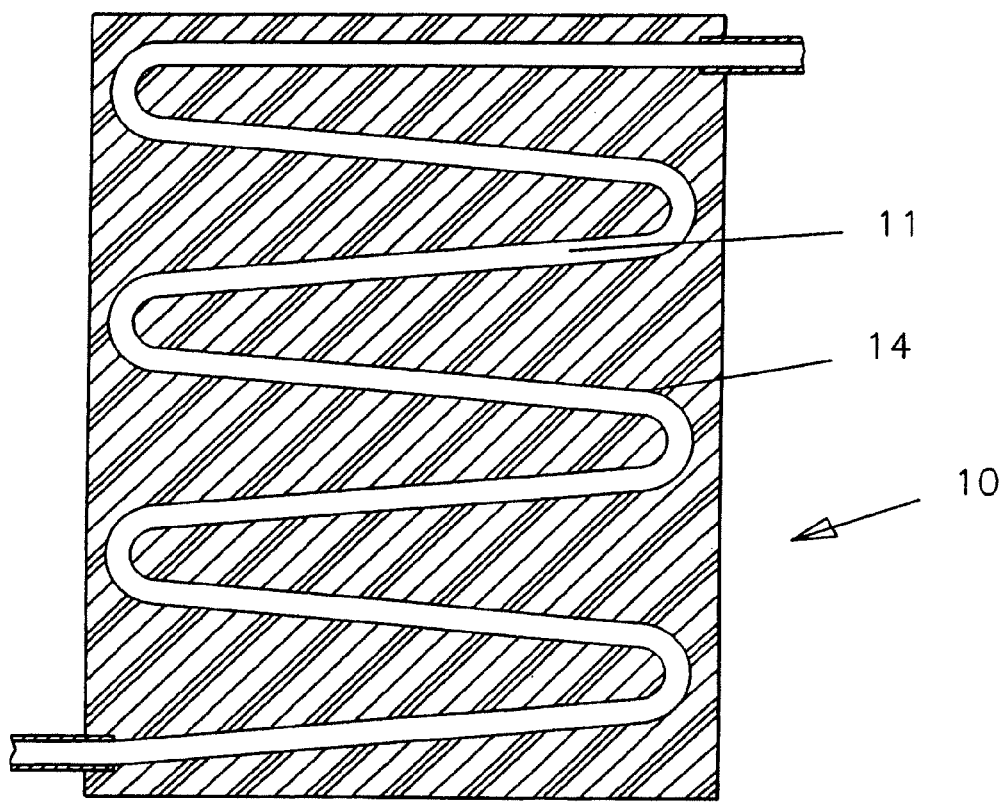
FIG. 3—Primary Warmer, Cross Section View

FIG. 3 illustrates The Primary Warmer 10. This warmer is made of two films that are sealed along weld lines 14 to form a winding path 11 for the infusate. The primary warmer is connected on the upstream side to the transfer set 140, where the cold blood flows through by gravity from the hanging blood bags. In some applications where high blood flow rates are required, pressure cuffs are used to squeeze the blood bags and accelerate the flow. The primary warmer is connected on the downstream side to the Intravenous Line 30. The winding path 11 inside the primary warmer is made long enough to ensure the blood is heated to normal body temperature as it completes its passage through the winding path. The winding path 11 is made wide enough to prevent any resistance to the infusate flow.

Figure 4:
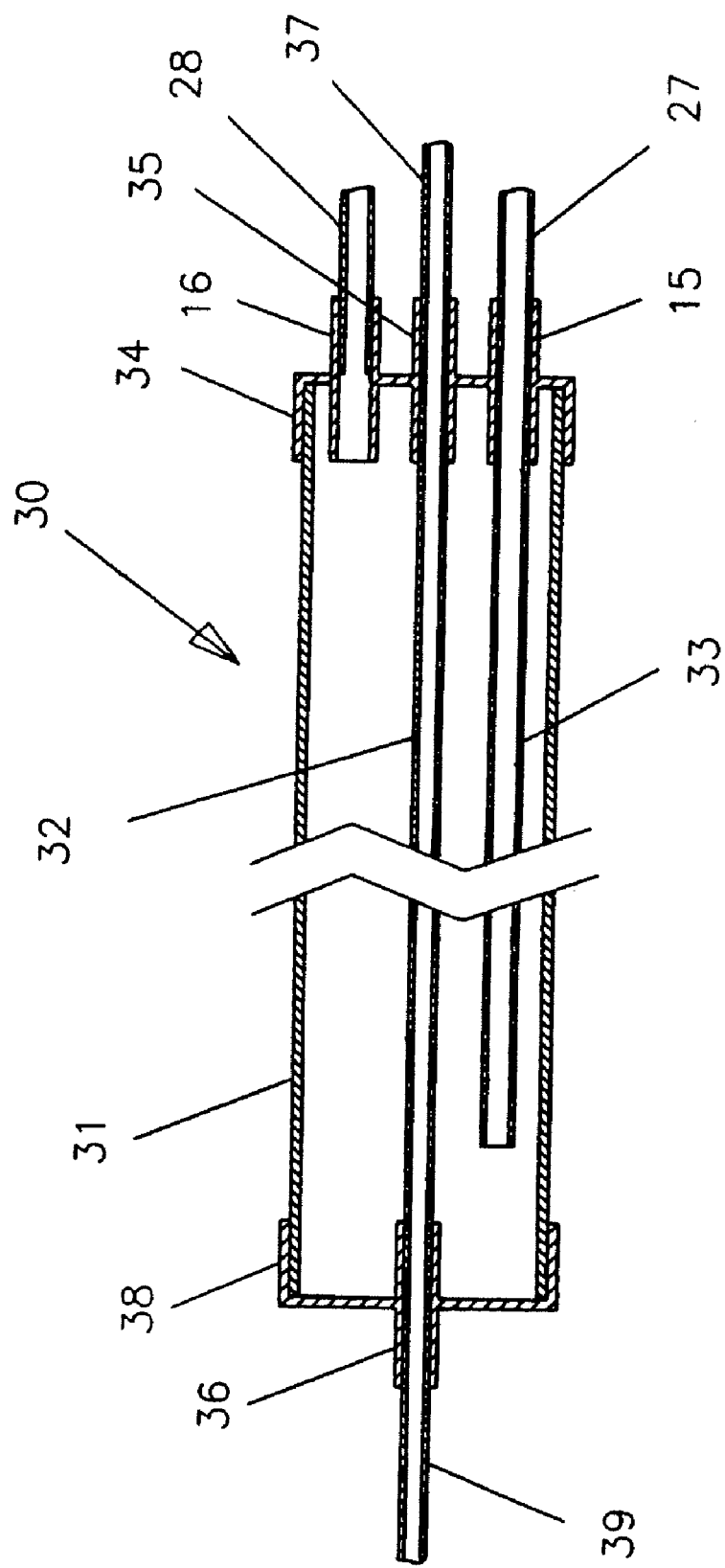
FIG. 4—Intravenous Line Heat Exchanger, Cross Section View

FIG. 4 illustrates a longitudinal cross section view of the Intravenous Line Heat Exchanger 30. The intravenous line comprises an outer tube 31 that is sealed by special caps at both ends. A blood carrying tube 32 penetrates the proximal end cap 34, extends longitudinally inside the outer tube, and exits the distal end cap 38. A warming fluid tube 33 is inserted inside the outer tube, penetrating the proximal end cap 34 and extending along the blood carrying tube 32 with its distal end open to the interior of the outer tube. The warming fluid tube is used to introduce the warming fluid inside the outer tube or to retrieve it from.

Cap 34, as shown in FIG. 4, has special ports that can be connected to tubing on either side of the cap therefore allowing for fluid flow through the cap. Port 35 is connected to tubing 32 on the inside of the intravenous line. The same port 35 is connected to tubing segment 37 on the outside. Tubing 37 provides the blood flow from the primary warmer 10 to the intravenous line 30. Cap 34 has two additional ports 15 and 16. These ports channel the warming fluid in and out of the intravenous line. Port 15 is connected to tubing 33 on the inside of the intravenous line. The same port is connected to tubing segment 27 on the outside of the intravenous line. The other end of tubing 27 is connected to a warming fluid chamber such as hot air compartment or wet fluid pouch. This tubing provides the warm fluid flow to the intravenous line. Port 16 is free on the inside and it is connected to tubing segment 28 on the outside of the intravenous line. The other end of tubing 28 is connected to the warming fluid chamber to retrieve the depleted warming fluid back to the warming pouch.

The outlet cap 38, shown in FIG. 4, seals the end of the outer tubing 31 at the patient side. This cap has a special port 36 that is connected to tubing 32 on the inside of the intravenous line. The same port is connected to tubing segment 39 that provides warm blood to the infusion site. The blood flows from the primary warmer through tubing 37, enters the intravenous line 30 through port 35 on cap 34, flows through tubing 32 where it is heated inside the intravenous line. The warm blood exits the intravenous line through port 36 on cap 38, then it flows to the patient through tubing 39.

Figure 5:
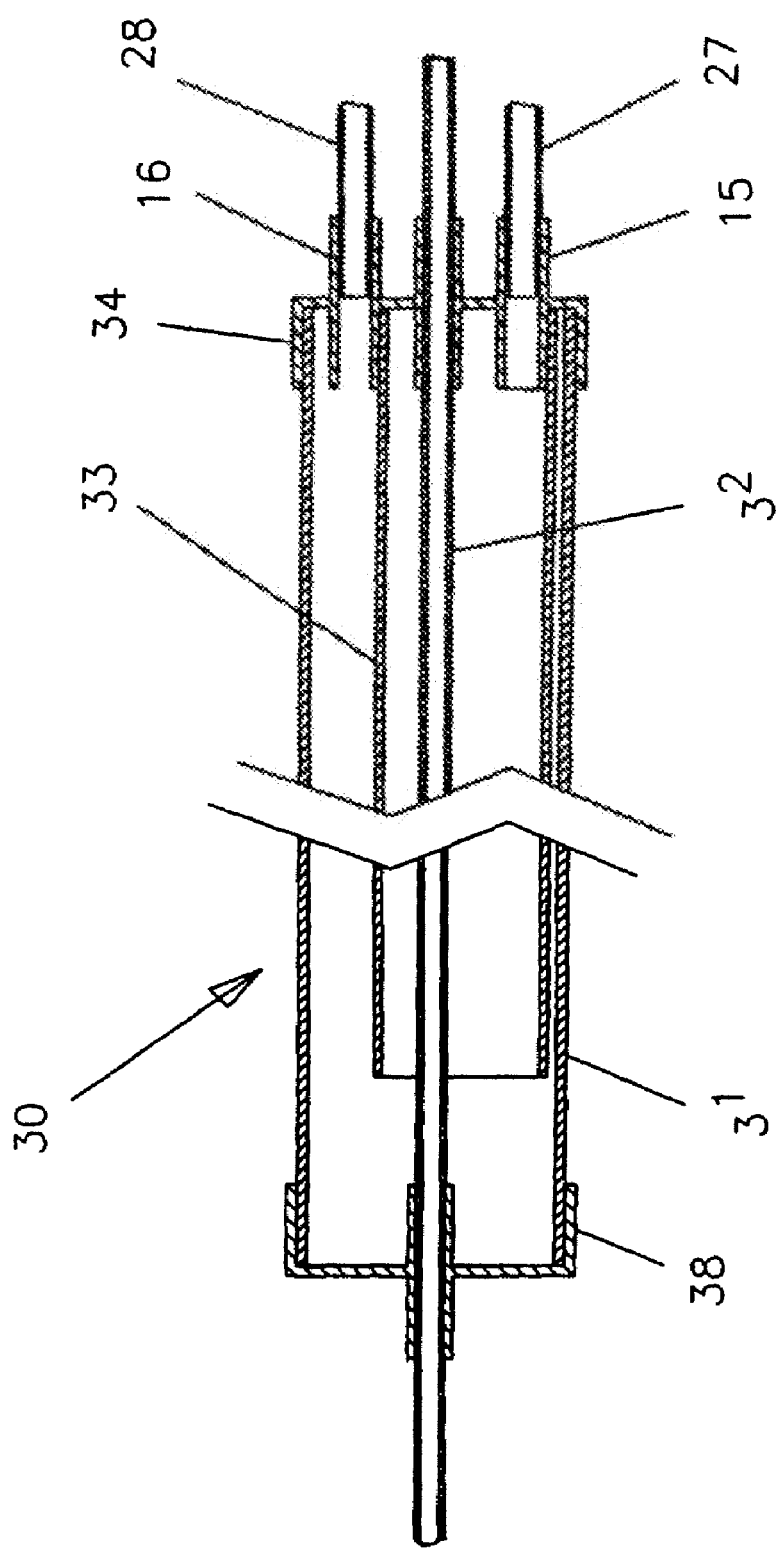
FIG. 5—Different Embodiment Intravenous Line Heat Exchanger, Cross Section View FIG. 6—Air Warming Chamber, Cross Section View FIG. 7—Blood Warming Disposable Set with Reusable Pouch, Schematic View FIG. 8—Pouch Heating Chamber, with Pouch mounted inside the chamber FIG. 9—Different Embodiment Intravenous Line Heat Exchanger, Seal Welded Ends

In another embodiment as shown in FIG. 5, the blood carrying tube 32 extends inside the warming fluid tube 33. In this arrangement the blood flows in the same direction as the warming fluid realizing a parallel flow heat exchanger. The blood carrying tube 32 is protected inside the warming fluid tube 33 and it is exposed to the warming fluid directly as it enters the intravenous line 30.

Figure 9:
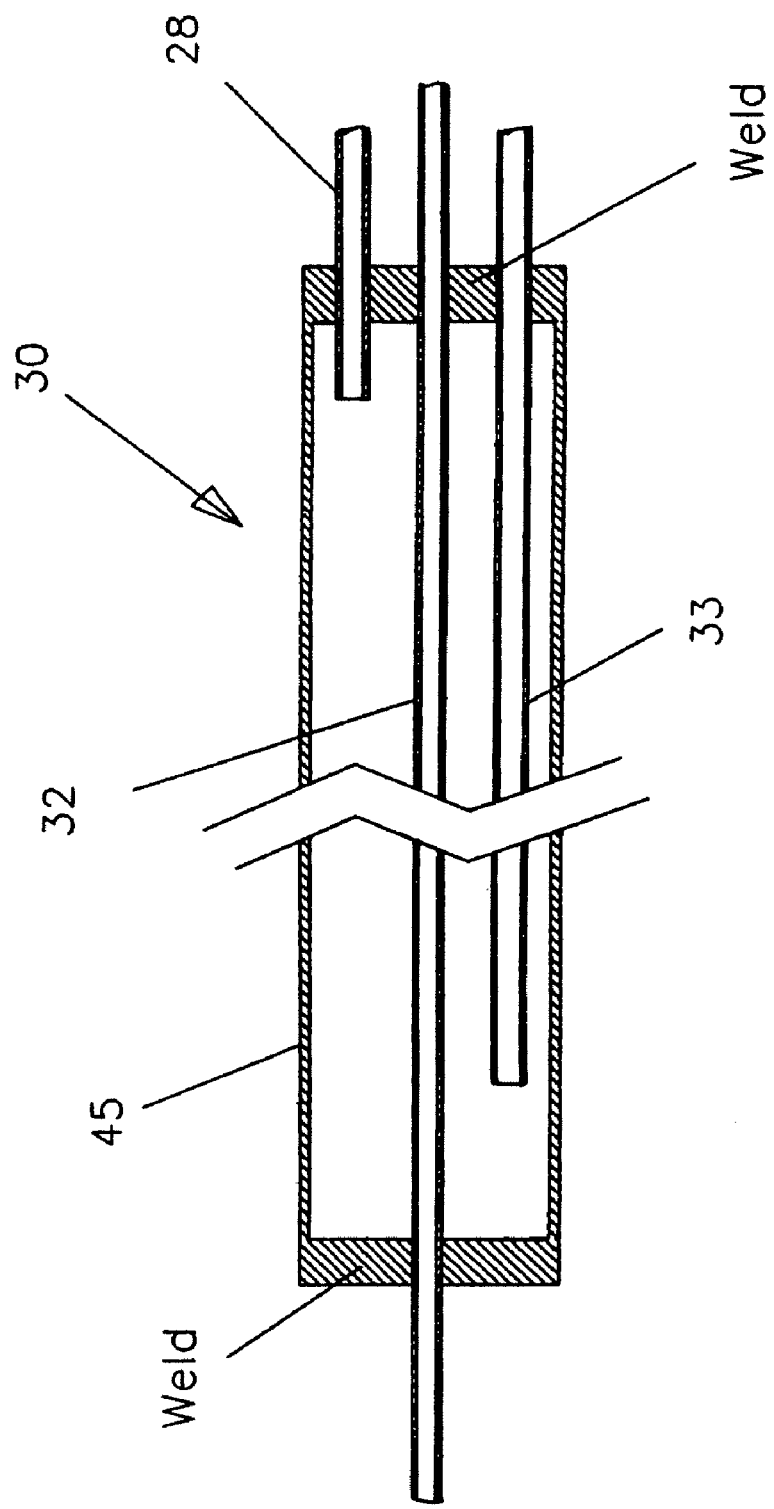

In another preferred embodiment shown in FIG. 9, a hose 45 made of flexible film material replaces the outer tube. A conduit constructed by extruding or seemingly welding films to have a thin wall hose. The hose cross section is built wide enough to comfortably accept blood carrying tube 32 and warming fluid tubes 33 and 28. The ends of the hose can be welded in a way to seal the conduit and to permit the blood carrying tube and the warming fluid tubes to penetrate through the sealed ends. The advantage of this embodiment is that no end caps are required and therefore, reduces the cost of the intravenous heat exchanger. It should be clear in this teaching that a thin wall tube can be utilized for the same purpose if the tubing can be seal welded at least at one end. Also should be clear that a hose conduit can be used to replace the blood carrying tube and the warming fluid tube in the intravenous heat exchanger.

Figure 6:
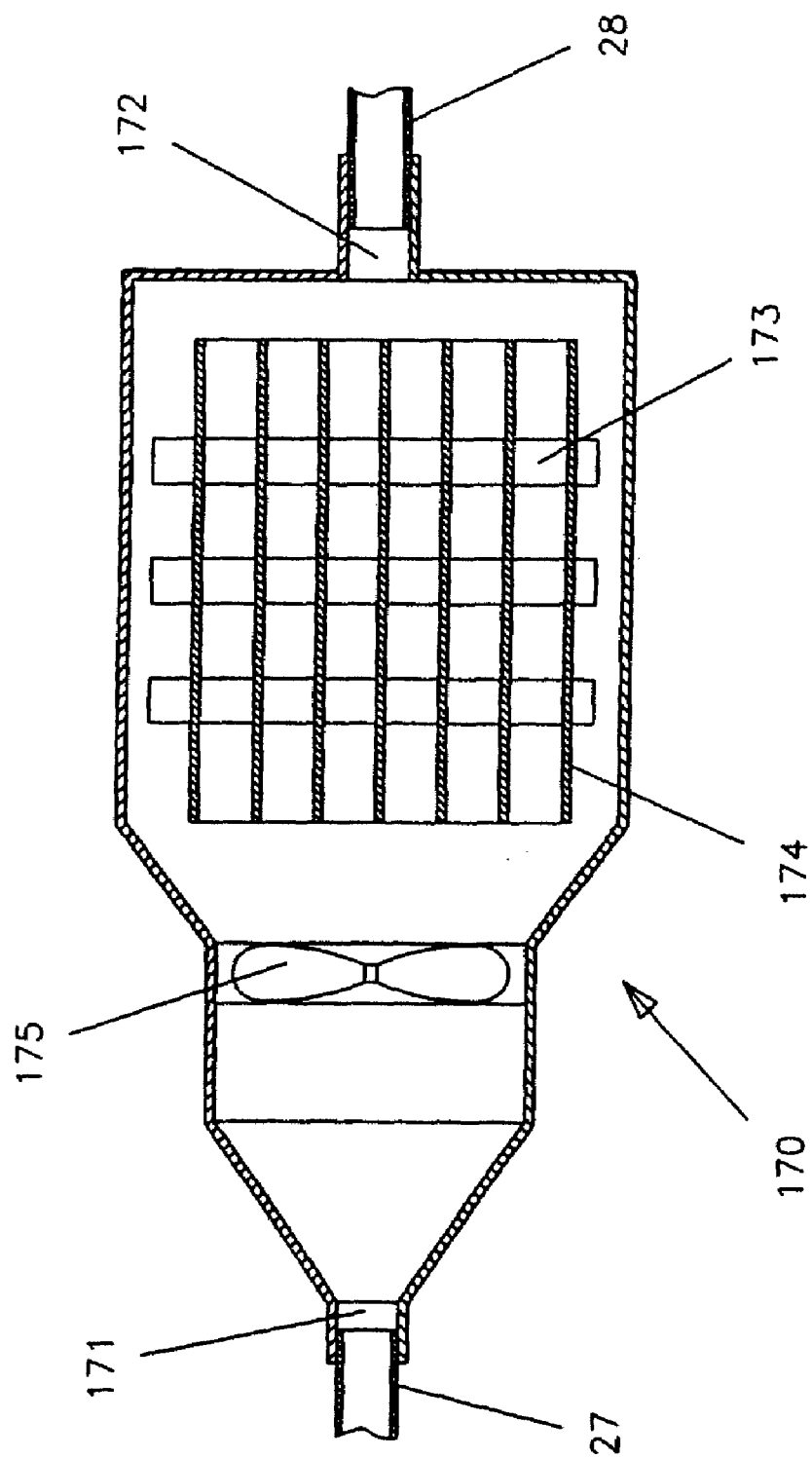

In the preferred embodiment, air is used to warm the infused blood inside the intravenous line. As shown in FIG. 6, the air is heated inside a closed compartment 170 having electrical heating elements 173 and fins 174. The compartment has an exit port 171 and an inlet port 172 connected to the intravenous line. An air fan 175 embedded at the exit port 171 of the air compartment drives the heated air through tubing 27 connected to the intravenous line 30 through port 15 on cap 34 (see FIG. 4). The air flows inside the warming fluid tube 33 and it is discharged at the distal end inside the outer tube 31 in the vicinity of cap 38. The hot air flows inside tubing 31 in the opposite direction to its flow inside tubing 33. It flows passing by the blood carrying tube 32 through the whole length of the intravenous line, hence warming the blood inside. Heat is transferred from the hot air to the blood to maintain it at its normal temperature. The hot air acts as a thermal barrier preventing any heat loss from the blood to the environment. Although a considerable amount of heat is lost from the air to the environment, the blood is maintained at its normothermic temperature by re-circulating warmed air. The thermally depleted air exits the proximal end of the intravenous line through port 16 on cap 34. The air is recirculated back to the warming fluid chamber through tubing 28 that is connected to the inlet port 172 of the air compartment.

Figure 7:
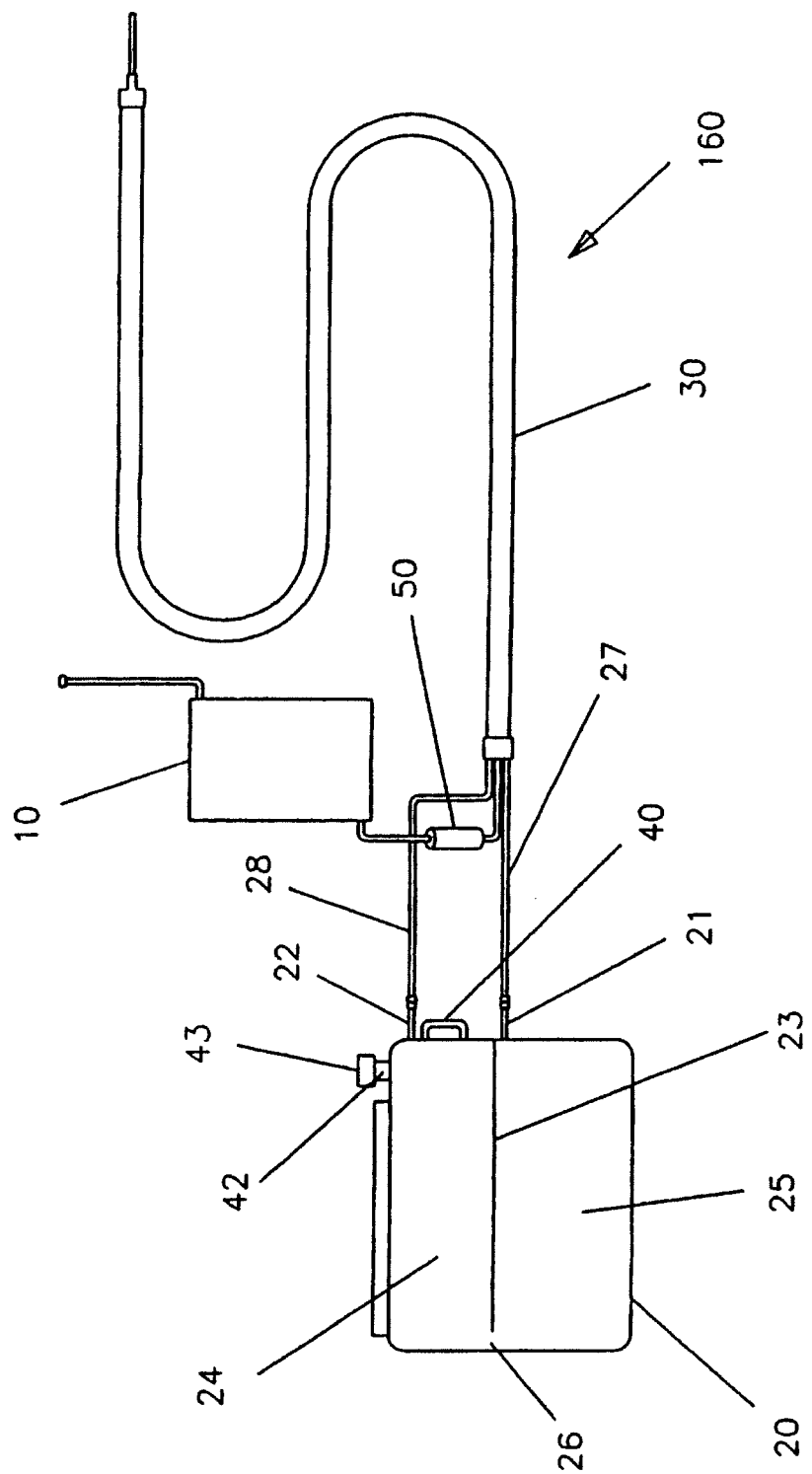

In another preferred embodiment, wet fluid such as water is used to warm the blood inside the intravenous line. FIG. 7 demonstrates a disposable set 160 with integrated warming fluid Pouch 20. The water is warmed inside the pouch and it is pumped in a closed circuit to flow inside the intravenous line 30 and returns back to the pouch 20. The pouch is composed of two films welded together to form at least two chambers 24 and 25, separated by divider or sealed weld line 23. These two chambers are filled with warming fluid. The weld line extends on a portion of the pouch allowing for a channel 26. This channel permits fluid flow between chambers 24 and 25. Chamber 24 is equipped with inlet port 22 and chamber 25 is equipped with outlet port 21. These ports allow for connection of tubes to channel the warming fluid from the pouch to the intravenous line 30 and back to the pouch. A transparent D-shaped channel 40 used to indicate the level of warming fluid inside the pouch.

The Pouch 20 is preferably made of material with high thermal conductivity such as Aluminum to facilitate the warming of the fluid inside the pouch. The pouch is designed with a capacity to hold enough fluid for blood warming. The pouch capacity can extend from 50 ml to 50 liters; in this application will be about 1.5 liters. The pouch is mounted inside the Blood Warming Device 100 and sandwiched between two plates maintained at a selective temperature. The water is warmed each time it passes through the pouch and loses heat to the blood each time it passes through the intravenous line. A peristaltic pump is used to circulate the water in a closed circuit encompassing the pouch and the intravenous line.

In another preferred embodiment, an air trap chamber 50 (shown in FIG. 7) is installed in line on the infusate carrying tube as it exits the primary warmer 10, and before it goes into the intravenous heat exchanger 30. The air trap chamber separates air bubbles from the infusate allowing only the fluid to pass through. Thus it prevents any air bubble that could have been mixed with the infusate from being infused into the patient's venous. As the flow of the infusate continues, the volume of the trapped air increases. The chamber being at a rigid and constant volume, the trapped air pressure is increased. When the pressure of the air reaches a certain level, a filtered orifice is activated to permits the air to escape out of the chamber. The orifice could also be activated by the system in response to a signal from a pressure sensor, an optic fluid level sensor, or an ultrasonic sensor.

In a different embodiment, the pouch is reused for limited number of operations provided that the rest of the disposable set is replaced for each use. The pouch has an opening 42 that provides means of access for warming fluid to be added the pouch. Warming fluid is added to the pouch to makeup for the lost fluid inside the discarded intravenous line after each use. Cap 43 is used to seal the opening 42 and prevent any fluid leak. Cap 43 can be easily removed from the opening 42 to fill the pouch with fluid.

Figure 8:
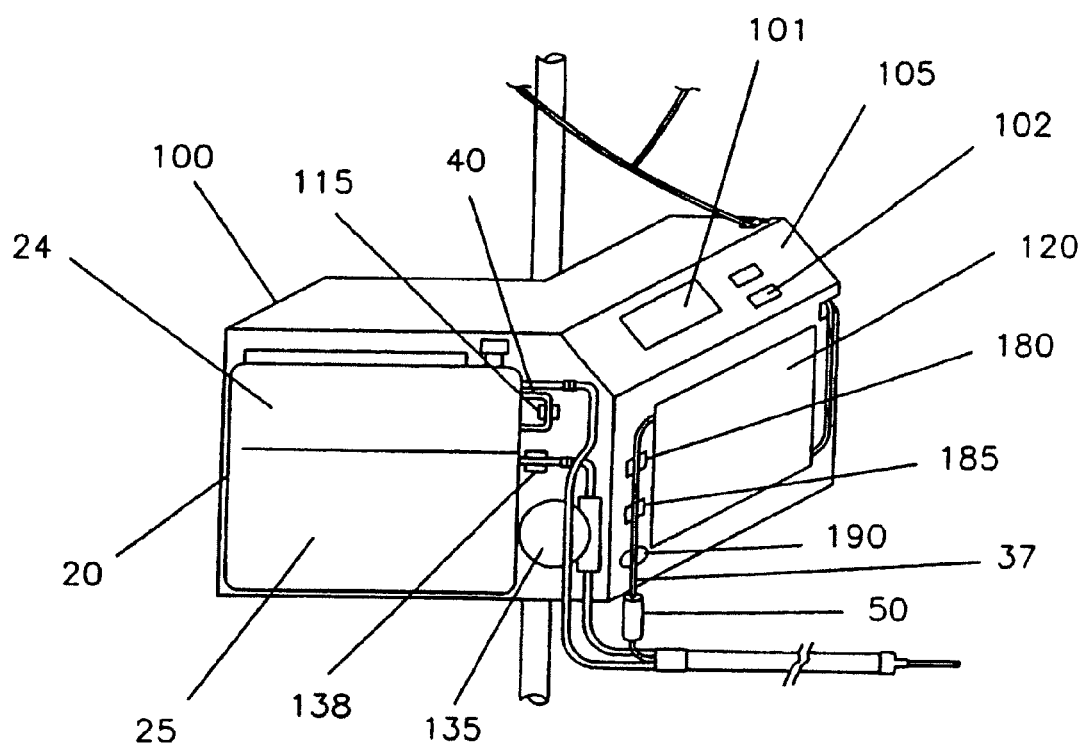

FIG. 8 illustrates the Warming Fluid pouch 20 mounted inside a Blood Warming Device 100. A Peristaltic pump 135 is used to circulate the warming fluid from the pouch to the intravenous line and backward. Tubing 28 that channels the warming fluid from the pouch to the intravenous line, is engaged with the peristaltic pump between the rotor and platen.

Temperature Sensor 138 is used to monitor the temperature of the warming fluid as it exits the fluid warming pouch. The temperature readout is communicated to a control system that gradually modifies the temperature of the warming pouch chamber to adjust the temperature of the warming fluid. The control system monitors the temperature of the infused fluid communicated by the IR sensor 180. The speed of the warming fluid pump is adjusted according to the infused fluid temperature. If the temperature of the infused fluid as it exits the Primary Warmer is low, the speed of the warming fluid pump increases to deliver higher heat capacity to the intravenous line heat exchanger. If the temperature of the infused fluid is high, the speed of the warming fluid pump decreases to deliver lower heat capacity to the intravenous line heat exchanger.

A transparent channel 40 is engaged with a fluid level sensor 115 mounted on the Warming Device 100. The fluid level sensor is used to indicate the warming fluid level in the pouch and informs the operator when the fluid level is low.

In a different embodiment, a connecting tube replaces the primary warmer 10. The primary warmer is completely discarded from the disposable sets 150 and 160. The connecting tube transfers the cold infusate from the source bag directly to the intravenous line heat exchanger 30. The infused fluid is warmed solely by the intravenous line heat exchanger.

The Blood Warming Device 100 is shown in FIGS. 1 and 8. The device is compact and lightweight. It is mounted on a standard IV-pole 103. The device has two heating chambers. A heating chamber used to primarily warm the blood is located on the front end of the device. This chamber has a door 120. When the door is opened, it allows for the mounting of the Primary Warmer 10 into the heating chamber. The second heating chamber is located on the side of the device and it is used to heat the warming fluid.

When air is used as a warming fluid, air-heating chamber is used to warm it. When wet fluid is used as warming fluid, a pouch containing fluid is mounted inside a heating chamber to warm the fluid inside the pouch.

The device has a control panel 105 with a display 101 to indicate infusate temperature and provide feedback to the user. The control panel also has push buttons or switches 102 to allow the user to control all the operations. A noninvasive Infra-Red (IR) temperature sensor 180 is used to monitor the warmed blood temperature. The IR sensor is mounted on the Blood Warming Device 100 and it is fitted to engage tubing 37 that connects the Primary Warmer 10 to the Intravenous Tubing 30. The IR sensor monitors the warmed blood temperature as it exits the primary warmer and passes through tubing 37. The IR sensor is passive and it accurately records the blood temperature without any physical contact with the blood. The IR sensor is connected to a computer on board of the Blood Warming Device 100 that posts the blood temperature on the display.

An ultrasonic air detector 185 used to detect air bubble in a fluid flow is mounted on the Blood Warming Device 100. The air detector is engaged with tubing 37 and monitors the blood flow inside the tubing. The air detector informs the operator when air bubbles are detected in the blood flow. A valve 190 is mounted on the Blood Warming Device 100. The valve is activated by the operator and used to stop the flow of the infused blood. The valve can be set to automatically stop the blood flow when certain volume of air is detected.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A system for warming blood or other biological fluids to a normal body temperature for infusion into a patient comprising;
    a blood warmer apparatus having a first compartment for heating a blood warming pouch and a second compartment for heating a warming fluid,
    the blood warming pouch defining a serpentine shaped passageway for blood flow therein, the pouch having an adaptable inlet for blood source connection, and an outlet suitably connected to an intravenous flow line; and
    an intravenous line heat exchanger to further warm blood as it flows to the patient, wherein the intravenous line heat exchanger has connecting tubes adapted to transport the warming fluid to flow inside the intravenous heat exchanger.

2. The system according to claim 1, wherein the warming fluid defines a gas such as air.

3. A system for warming blood or other biological fluids to a normal body temperature for infusion into a patient comprising;
    a blood warmer apparatus having a first compartment for heating blood warming pouch, a second compartment for heating a warming fluid enclosed in a container, and means to circulate the warming fluid;
    the blood warming pouch defining a serpentine shaped passageway for blood flow therein, the pouch having an adaptable inlet for blood source connection, and an outlet connected to an intravenous flow line;
    the container adapted to conduct enough heat to warm the warming fluid up to a temperature in the vicinity of 42° C.; and
    an intravenous line heat exchanger to further warm the blood as it flows to the patient, wherein the intravenous line heat exchanger has connecting tubes adapted to transport the warming fluid to flow through the intravenous heat exchanger and to circulate back to the warming fluid container.

4. The system according to claim 3, wherein the warming fluid container has means to add more fluid.

5. The system according to claim 3, further including means to determine fluid level inside the warming fluid container.

6. The system according to claim 3, further including a peristaltic pump to drive the warming fluid from the warming fluid container, flow through the intravenous heat exchanger, and re-circulate back to said warming fluid container.

7. The system according to claim 3, further including means to determine the warming fluid temperature.

8. The system according to claim 3, further including means to control the warming fluid temperature.

9. The system according to claim 3, further including means to control a flow rate for the warming fluid.

10. The system according to claim 3, wherein the warming fluid container defines a pouch having thermally conductive walls.

11. The system according to claim 1, wherein the Intravenous line heat exchanger comprises:
    an outer tube having opposing first and second sealed ends enclosing an interior space;
    a blood flow tube carrying blood or biological fluid extending longitudinally through the outer tube from the first sealed end to the second sealed end, wherein blood or biological fluid flows through the first tube from the first sealed end to the second sealed end; and,
    an input tube carrying warming fluid and sealably extending through one of the sealed ends of the outer tube, the input tube terminating in an open end communicating with the interior space of the outer hose such that the warming fluid flows out of the open end of the input tube and fills the interior space,
    an output tube sealably extending through one of the sealed ends of the outer tube, the output tube terminating in an open end communicating with the interior of the interior space, the warming fluid exiting the interior space through the open end of the output tube.

* * * * *